(12) United States Patent
Chen et al.

(10) Patent No.: US 9,795,588 B2
(45) Date of Patent: Oct. 24, 2017

(54) MAMMALIAN TOR INHIBITOR

(71) Applicant: Chang Gung University, Taoyuan (TW)

(72) Inventors: Chin-Chuan Chen, Taoyuan (TW); Yann-Lii Leu, Taoyuan (TW); Shu-Huei Wang, Taoyuan (TW)

(73) Assignee: Chang Gung University, Taoyuan (TW)

( * ) Notice: Subject to any disclaimer, the term of this patent is extended or adjusted under 35 U.S.C. 154(b) by 0 days.

(21) Appl. No.: 15/226,128

(22) Filed: Aug. 2, 2016

(65) Prior Publication Data

US 2017/0231947 A1     Aug. 17, 2017

(30) Foreign Application Priority Data

Feb. 16, 2016 (TW) .............................. 105104459 A

(51) Int. Cl.
*A61K 31/352* (2006.01)
*A61K 36/487* (2006.01)

(52) U.S. Cl.
CPC .......... *A61K 31/352* (2013.01); *A61K 36/487* (2013.01)

(58) Field of Classification Search
None
See application file for complete search history.

(56) References Cited

U.S. PATENT DOCUMENTS 6,294,538 B1 * 9/2001 Mylari ................. A61K 31/505
514/252.14

OTHER PUBLICATIONS

Kamboj, J. et al., J. Health Science 2011 vol. 57 pp. 225-235.*
Shim, S.H. et al., J. Kor. Soc Appl. Biol. Chem. 2009 vol. 52 pp. 568-572.*

* cited by examiner

*Primary Examiner* — Heidi Reese
(74) *Attorney, Agent, or Firm* — Muncy, Geissler, Olds & Lowe, P.C.

(57) ABSTRACT

A method for inhibiting mammalian TOR in a cell, comprising: providing a compound of formula (1):

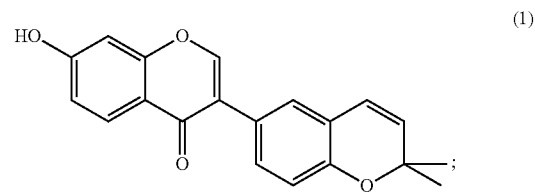

and incubating the cell with the compound. Also provided is a method for extending life span of a subject, comprising: providing the compound; and administering the compound to the subject. Yet also provided is a method for treating a mammalian TOR activation-caused disease in a subject, comprising: providing the compound; and administering the compound to the subject.

3 Claims, 12 Drawing Sheets

MAMMALIAN TOR INHIBITOR

CROSS REFERENCE

This non-provisional application claims priority from Taiwan Patent Application No. 105104459, filed on 16 Feb. 2016, the content thereof is incorporated by reference herein.

FIELD OF THE INVENTION

The present invention relates to an inhibitor, and more particularly to a mammalian TOR inhibitor.

BACKGROUND OF THE INVENTION

Mammalian TOR, also called "mTOR" or "mammalian target of rapamycin", is a serine/threonine protein kinase, and can regulate cellular growth, proliferation, migration, survival, protein synthesis, autophagy, and transcription.

Up to now, there exist several mTOR inhibitors, such as epigallocatechin gallate (EGCG), caffeine, curcumin, resveratrol, rapamycin, temsirolimus, everolimus, and ridaforolimus. Therefore, it is desirable to develop a novel mTOR inhibitor for the application in the bioregulation and the treatment of related diseases.

SUMMARY OF THE INVENTION

An objective of the present invention is to provide a method for inhibiting mammalian TOR in a cell. The method comprises:

providing a compound of formula (1):

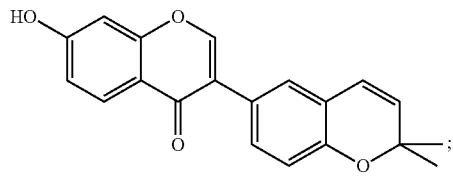

and
incubating the cell with the compound.

Another objective of the present invention is to provide a method for extending life span of a subject. The method comprises:

providing a compound of formula (1):

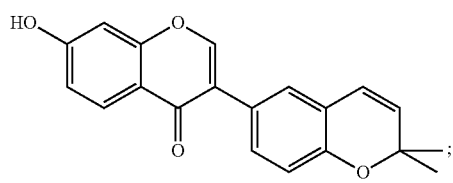

and
administering the compound to the subject.

Another objective of the present invention is to provide a method for treating a mammalian TOR activation-caused disease in a subject. The method comprises:

providing a compound of formula (1):

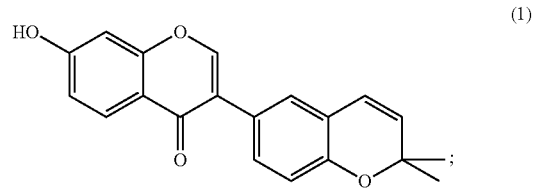 [SMILES: CC1(C)C=Cc2cc(-c3coc4cc(O)ccc4c3=O)ccc2O1]

and
administering the compound to the subject.

DETAILED DESCRIPTION OF THE INVENTION

The detailed description and preferred embodiments of the invention will be set forth in the following content, and provided for people skilled in the art so as to understand the characteristics of the invention.

In the present invention, a compound of formula (1) isolated from *Psoralea corylifolia* can lengthen cell lifespan. According to this, the present invention also discloses the compound can inhibit mammalian TOR. It is noted that the formula (1) is represented as:

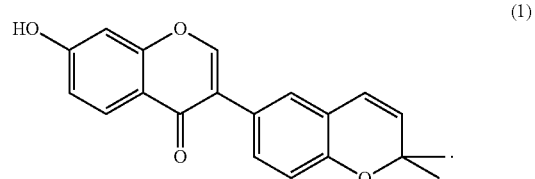

This compound is scientifically named corylin. If not expressly indicated otherwise in the following description, the terms "a compound of formula (1)" and "corylin" used in the content are intended to convey the same meaning.

A first embodiment of the present invention discloses a method for inhibiting mammalian TOR in a cell, and the method comprises: providing corylin; and incubating the cell with the corylin. Generally, the corylin may be obtained via chemical synthesis or extracted from nature, e.g. extraction from *Psoralea corylifolia*.

A second embodiment of the present invention discloses a method for extending life span of a subject, and the method comprises: providing corylin; and administering the corylin to the subject. In other words, the corylin can be in the form of medicine to be administered to the subject. Further, the corylin can inhibit mammalian TOR in the subject, so that his/her life span can be extended. Moreover, the corylin can be obtained via chemical synthesis or extracted from nature, e.g. extraction from *Psoralea corylifolia*.

A third embodiment of the present invention discloses a method for treating a mammalian TOR activation-caused disease in a subject, and the method comprises: providing corylin; and administering the corylin to the subject. An example of the disease is, but not limited to, cardiovascular disease, obesity, or diabetes. In other words, the corylin can be in the form of medicine to be administered to the subject. Further, the corylin can treat the disease by inhibiting mammalian TOR. The corylin can be obtained via chemical synthesis or extracted from nature, e.g. extraction from *Psoralea corylifolia*.

The following examples are offered to further illustrate the present invention:

Example 1

Extraction of Corylin

Figure 1:
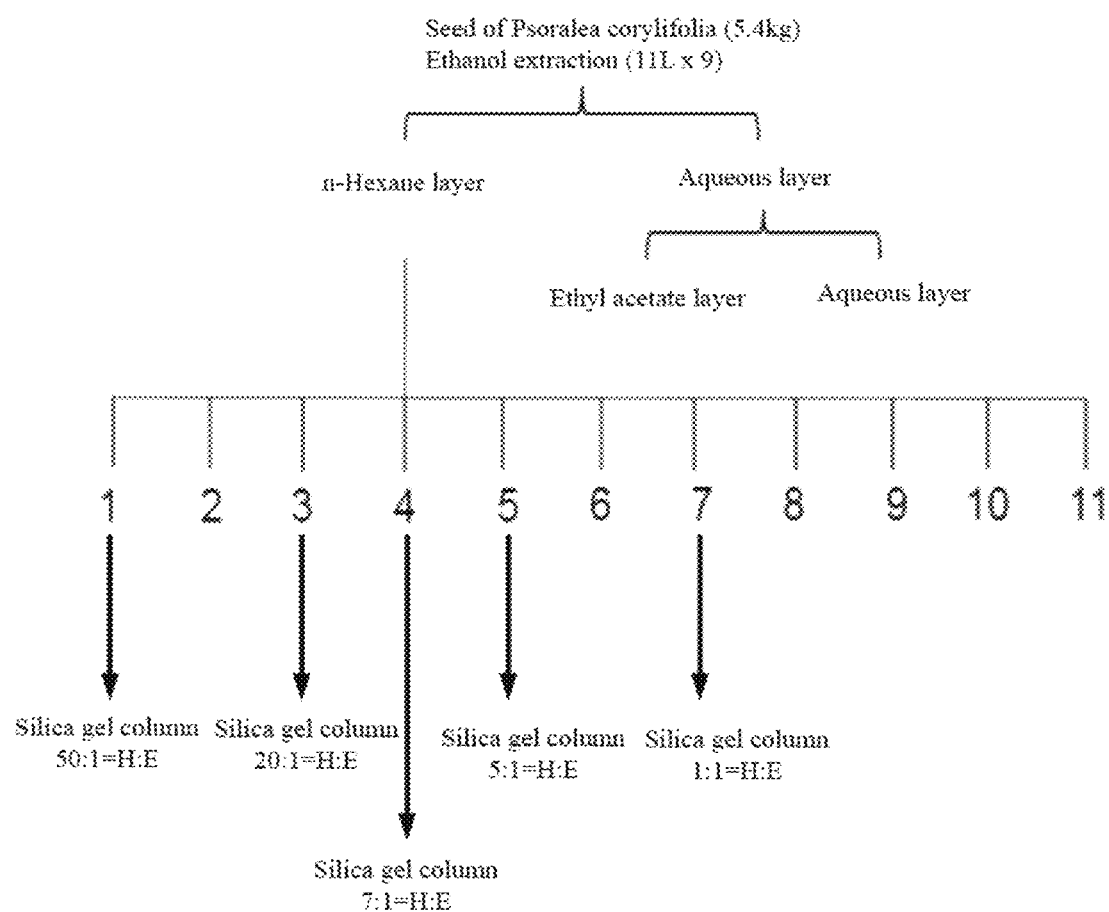
FIG. 1 is a chart illustrating the extraction of corylin from *Psoralea corylifolia*.

As shown in FIG. 1, *Psoralea corylifolia* seeds (5.4 kg) were pulverized, and then the pulverized seeds were extracted with ethanol. In the extraction process, the pulverized seeds were coldly soaked in 11 L ethanol for 4 times, and hotly soaked in 11 L 70° C.—ethanol for 4 hours for 5 times. After filtering the extract, the filtered extract was concentrated. The concentrated extract was partitioned with n-hexane and water to obtain an n-hexane layer and an aqueous layer. The aqueous layer was further partitioned with ethyl acetate to form an ethyl acetate layer and another aqueous layer; the n-hexane layer was further applied on a silica gel column, and then eluted with an n-hexane/ethyl acetate mixture in different concentration gradients to sequentially gain 11 fractions.

The first fraction was obtained with the elution of the n-hexane/ethyl acetate mixture in 50:1 and contained bakuchiol; the third fraction was obtained with the elution of the n-hexane/ethyl acetate mixture in 20:1 and contained isopsoralen; the forth fraction was obtained with the elution of the n-hexane/ethyl acetate mixture in 7:1 and contained psoralen; the fifth fraction was obtained with the elution of the n-hexane/ethyl acetate mixture in 5:1 and contained corylin; and the seventh fraction was obtained with the elution of the n-hexane/ethyl acetate mixture in 1:1 and contained psoralidin.

Example 2

Effect of Corylin on Cell Life Span

Figure 2:
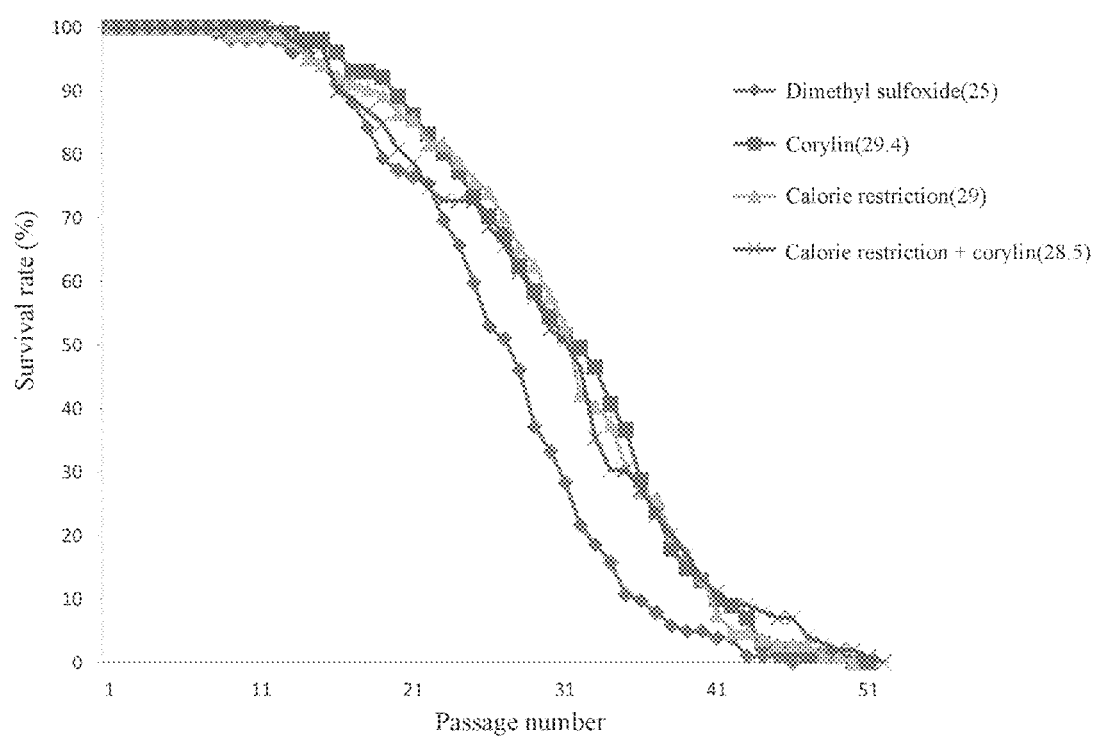
FIG. 2 is a graph illustrating the replicative life span of a corylin-treated yeast cell.

A yeast colony was selected and cultured in a YEPD culture media. When the OD value of the media was at 0.6-0.8, 20 µl of the media containing different chemicals was added to a YEPD solid media, and then 20-30 yeast cells were selected using a tetrad dissection microscope manipulation system. The selected yeast cells were cultured at 30° C. for 3-5 hours to divide into first generation yeast cells. Afterwards, the first generation yeast cells were cultured at 30° C. for 3-5 hours to divide into second generation yeast cells. The culturing step was repeated until final generation yeast cells which cannot divide anymore existed. Finally, the yeast cells' passage number was counted according to the total division number. As shown in FIG. 2, corylin can increase yeast cells' passage number.

Figure 3:
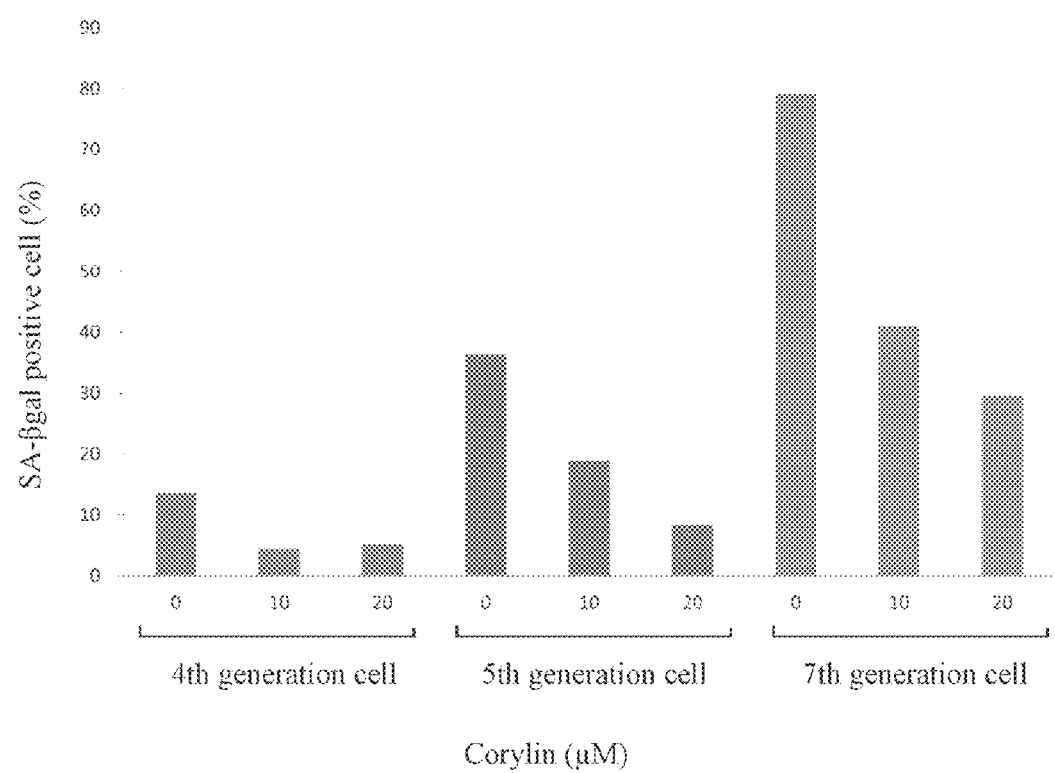
FIG. 3 is a graph illustrating the inhibition of cellular aging by corylin.

In addition, human umbilical vein endothelial cells (HUVEC) were treated with corylin in different concentrations, and the cells at this moment were called first generation cells. Second generation cells grew by culturing the first generation cells for 2-3 days, and then the second generation cells were treated with corylin in different concentrations. Third to Nth generation cells grew by repeating the culturing process. During each culture process, SA-βgal assay was used to analyze the responding generation cells. The more SA-βgal positive cells the cultured cells contained, the older the cultured cells were. As shown in FIG. 3, corylin can inhibit the cells' aging in dose-dependent manner.

As above, corylin can extend cell lifespan.

Example 3

Effect of Corylin on Mammalian S6K Phosphorylation

Figure 4:
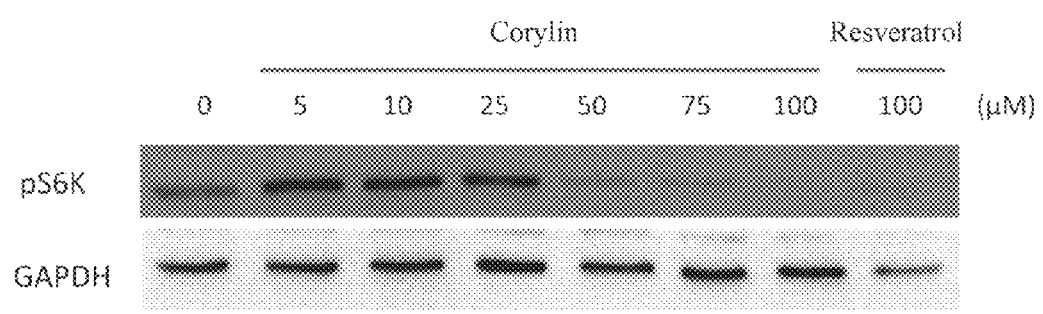
FIG. 4 is a Western blotting graph illustrating the inhibition of S6K phosphorylation by corylin.

Human osteosarcoma (U2OS) cells were treated with different chemicals in different concentrations. After the cells were cultured for 8 hours, the protein therein was extracted. Finally, Western blotting assay was used to analyze the extracted protein. As shown in FIG. 4, corylin can suppress S6K phosphorylation in dose-dependent manner.

Figure 5:
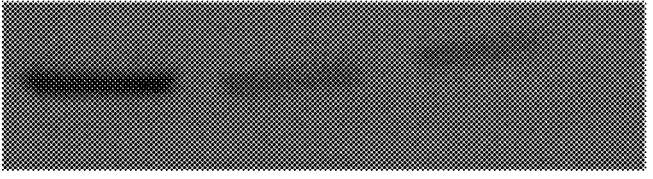
FIG. 5 is a Western blotting graph illustrating no interference between mammalian SIRT1 inhibitor EX-527 and S6K phosphorylation caused by corylin.

Moreover, human osteosarcoma cells were pre-treated with mammalian SIRT1 inhibitor EX-527 for 1 hour. Afterwards, those cells were treated with 100 µM corylin and cultured for 8 hours. Finally, Western blotting assay was used to analyze the protein extracted from those cells. As shown in FIG. 5, mammalian SIRT1 inhibitor EX-527 cannot interfere with the S6K phosphorylation caused by corylin.

Example 4

Effect of Corylin on Adipocytes Differentiation

Figure 6:
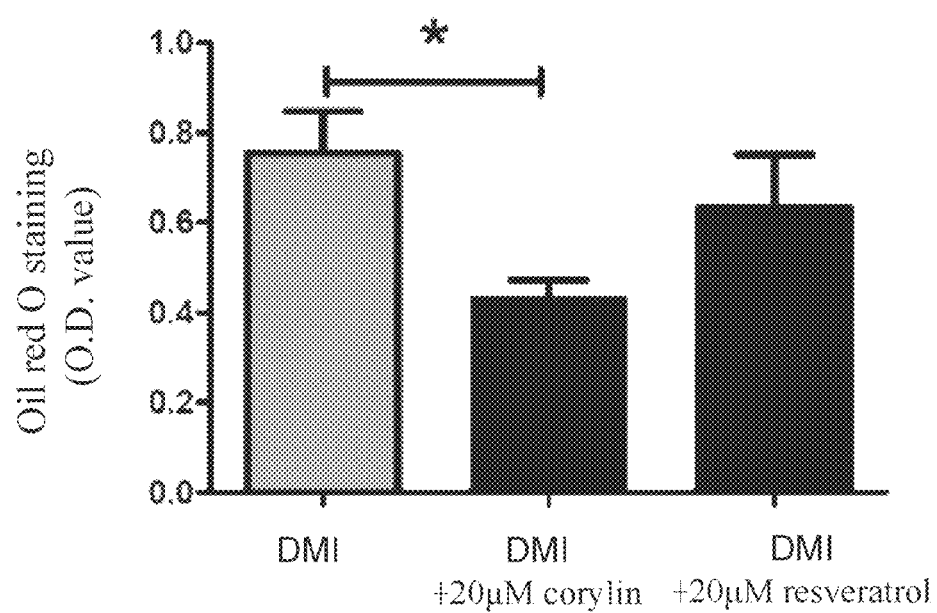
FIG. 6 is an oil-red O staining graph illustrating the inhibition of adipocyte differentiation caused by corylin.

Mouse adipocytes (3T3-L1) were co-treated with DMI (5 µM of dexamethasone, 0.5 mM of 3-isobutyl-1-methylxanthine, and 0.1724 mM of insulin) and different chemicals. After being cultured for 8 days, the cell media was removed and oil-red O staining was used to analyze these adipocytes' differentiation. As shown in FIG. 6, inhibition of adipocytes' differentiation caused by corylin is more obvious than that caused by resveratrol.

As above, corylin has function on weight loss.

Example 5

Effect of Corylin on S6K Phosphorylation Caused by Insulin

High concentration insulin can cause phosphorylation and thus cells are resistant to insulin, which is one cause for type II diabetes. In order to mimic type II diabetes, human osteosarcoma cells were cultured in 400 nM of insulin and different chemicals for 10 minutes. After which, Western blotting assay was used to analyze the protein in these cells.

Figure 7:
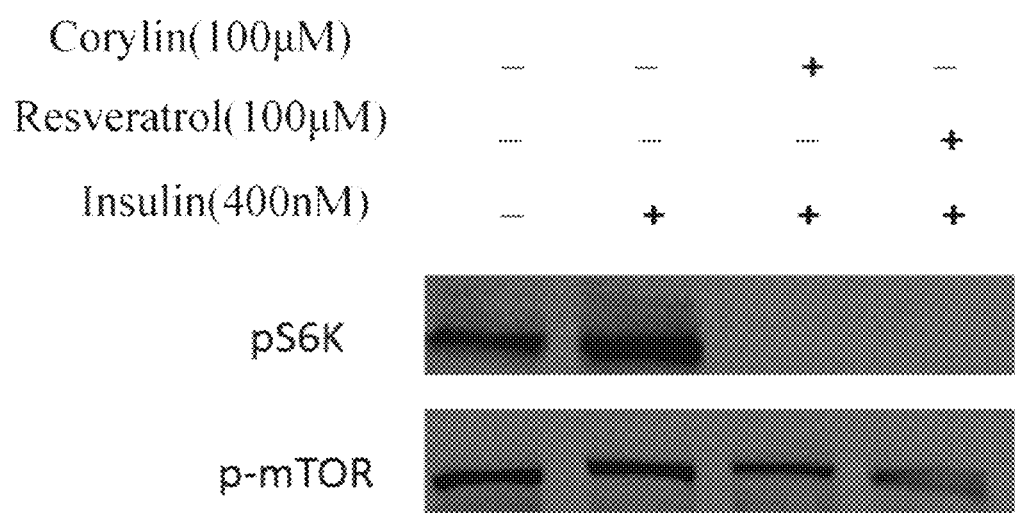
FIG. 7 is a Western blotting graph illustrating the suppression of insulin-induced S6K phosphorylation caused by corylin.

As shown in FIG. 7, insulin can induce S6K phosphorylation in cells, but corylin can suppress such phosphorylation caused by insulin.

As above, corylin has an effect on the treatment of diabetes, especially type II diabetes.

Example 6

Effect of Corylin on ICAM-1 Expression Caused by Lipopolysaccharide

Figure 8:
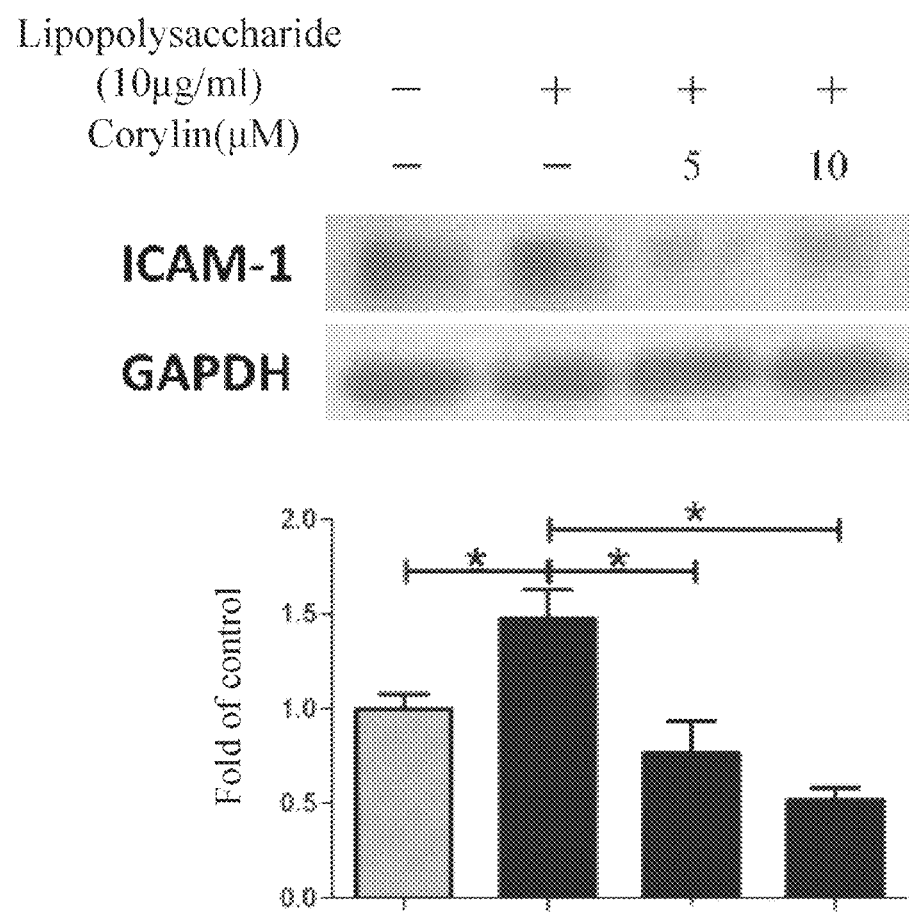
FIG. 8 is a Western blotting graph illustrating the inhibition of lipopolysaccharide-induced ICAM-1 expression by corylin.

Lipopolysaccharide can induce immune response on blood vessels. During immune response, blood vessels can also overexpress ICAM-1, which is one cause of cardiovascular disease. To mimic this disease, human aortic smooth muscle cells (HASMC) were treated with corylin in different concentrations and then cultured for 24 hours. After these cells were treated with lipopolysaccharide for 24 hours, the protein in these cells was extracted and analyzed by Western blotting assay. As shown in FIG. 8, corylin can inhibit ICAM-1 expression caused by lipopolysaccharide.

As above, corylin has effect on the treatment and/or prevention of cardiovascular disease.

Example 7

Figure 9:
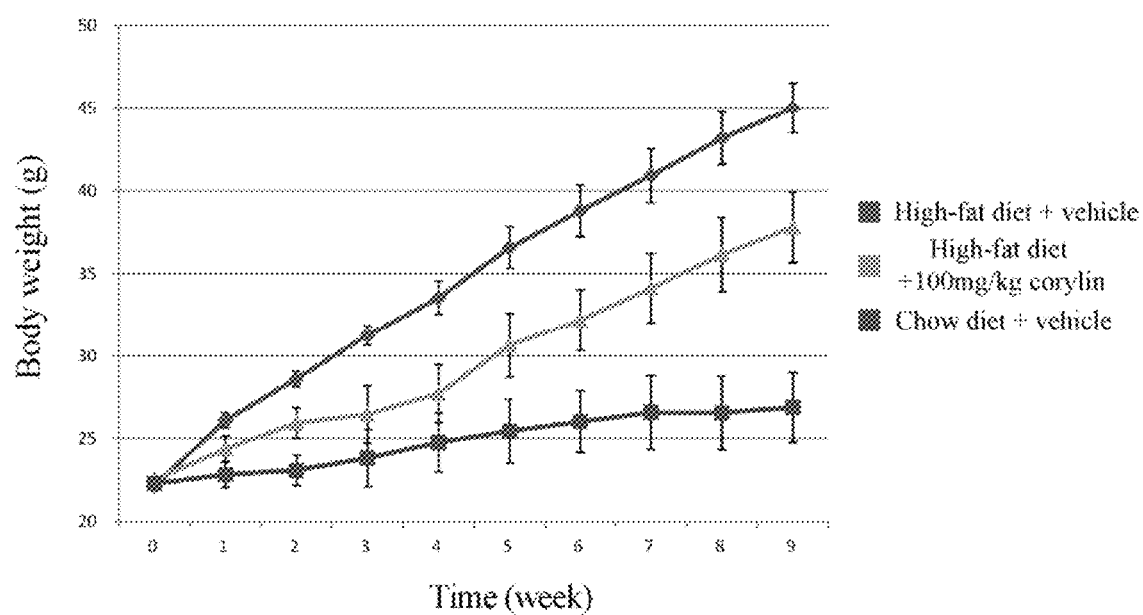
FIG. 9 is a graph illustrating the effect of corylin on the reduction of mice body weight.
Figure 10:
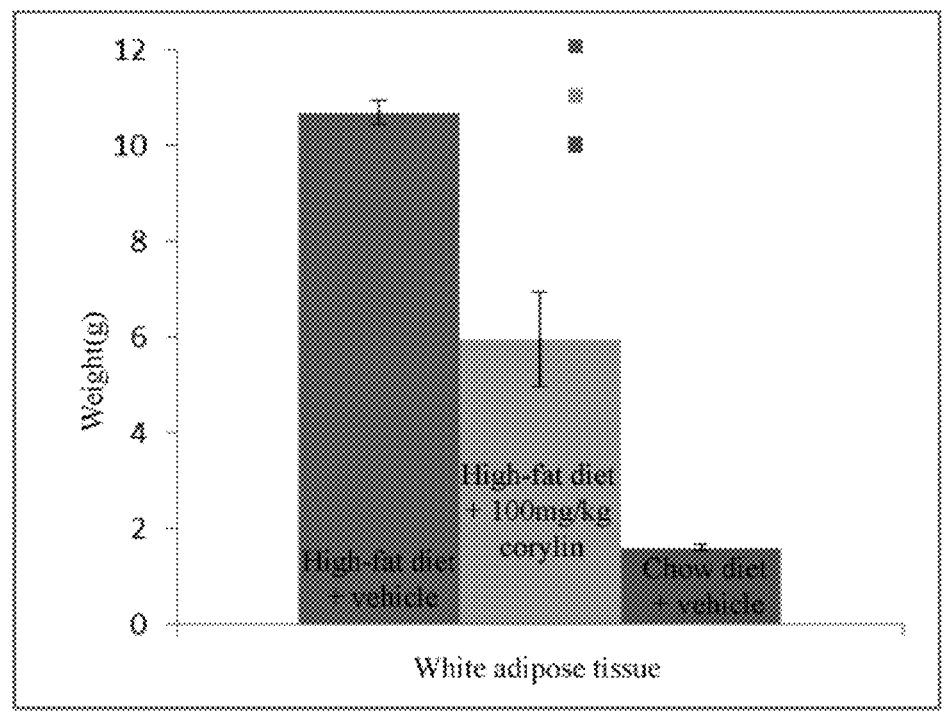
FIG. 10 is a graph illustrating the effect of corylin on the reduction of mice liver weight, and white adipocytes tissue weight.
Figure 11:
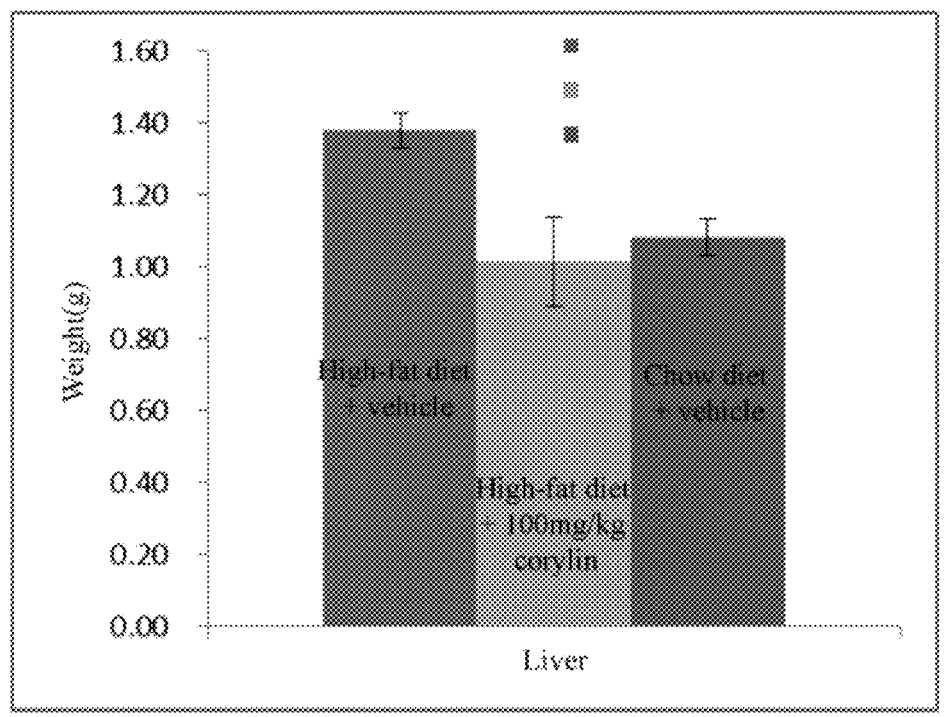
FIG. 11 is a graph illustrating the effect of corylin on the reduction of mice white adipocytes tissue weight.

Effect of Corylin on Obesity, Intraperitoneal Glucose Tolerance and Insulin Tolerance Animal experiments were performed and proved according to guidelines of Institutional Animal Care and Use Committee of Chang Gung University (IACUC; Approval No. CGU11-117). Male C57BL/6 mice (8 weeks old) were purchased from the National Laboratory Animal Center. Mice were divided into three groups (n=6 each group): chow diet; high-fat diet (HFD, 60% ResearchDiet, D12492); and HFD gavage with corylin at 100 mg/kg. To compare the metabolic effects of corylin, parameters such as body weights, liver weights and white adipocytes tissue (WAT) weights from epididymal, inguinal and axilla subcutaneous were measured at the end of the treatment. As shown in FIGS. 9-11, corylin has an effect on the reduction of body weight, liver weight, and white adipocytes tissue weight.

Figure 12:
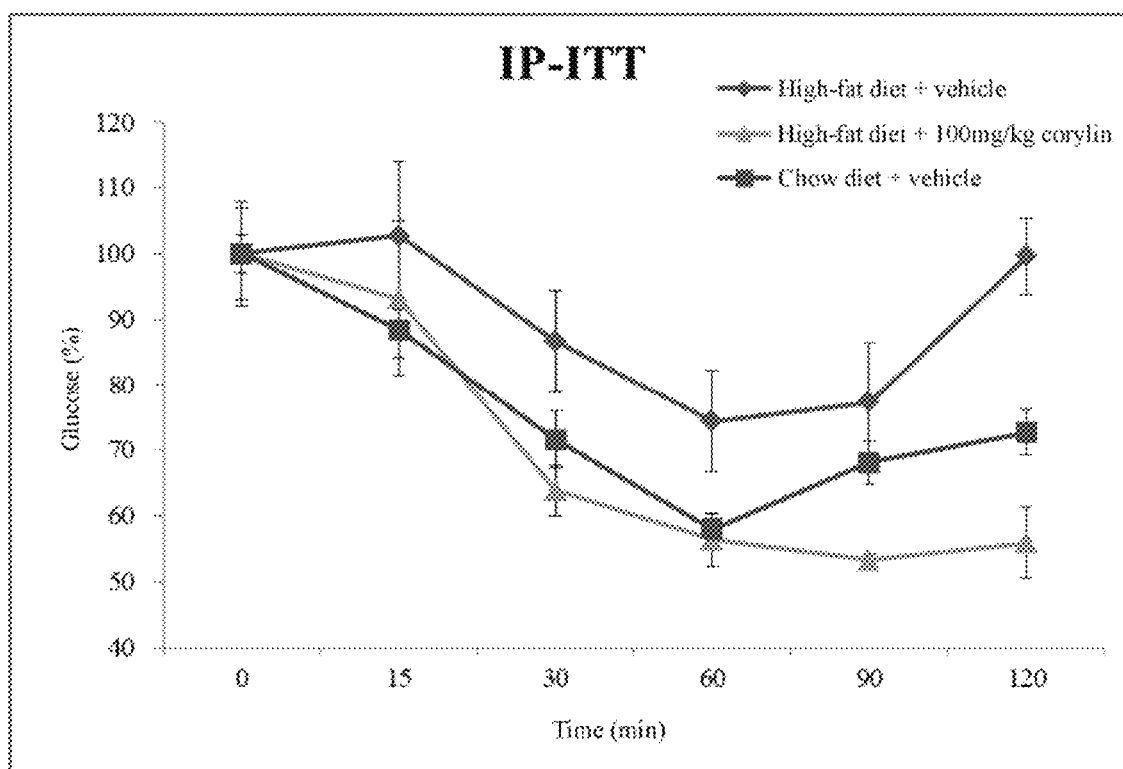
FIG. 12 is a graph illustrating intraperitoneal glucose tolerance of mice caused by corylin.
Figure 13:
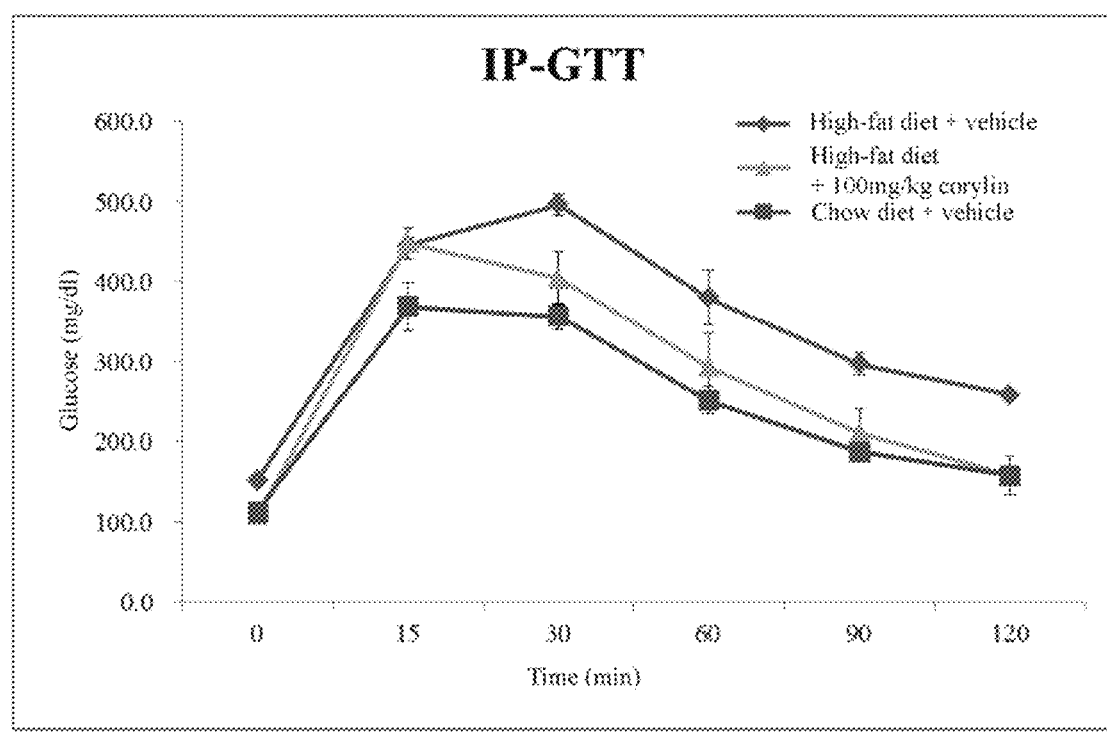
FIG. 13 is a graph illustrating insulin tolerance of mice caused by corylin.

For intraperitoneal glucose tolerance testing, mice were fasted for 16 hours and then injected with 2 g/kg of glucose solution. For insulin tolerance testing, mice were fasted for 3 hours and then injected with 1.2 U/kg insulin. Serum blood glucose levels were measured at 0, 15, 30, 60, 90, and 120 min after glucose and insulin injection. As shown in FIGS. 12 and 13, corylin can lower intraperitoneal glucose tolerance and insulin tolerance on animals.

As described above, corylin can inhibit mammalian TOR, so it is potential to be a mammalian TOR inhibitor.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for inhibiting mammalian TOR in a cell, comprising:
providing a compound of formula (1):

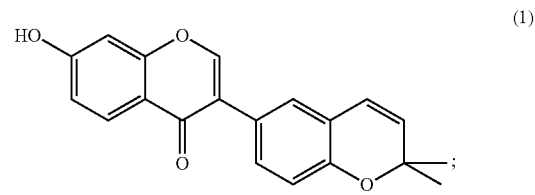 [SMILES: CC1(C)C=Cc2cc(-c3coc4cc(O)ccc4c3=O)ccc2O1]

incubating the cell with the compound.

2. The method as claimed in claim 1, wherein the compound is obtained via extraction from *Psoralea corylifolia*.

3. The method as claimed in claim 1, wherein the compound activates a downstream factor of mammalian TOR.

* * * * *